United States Patent
Kim et al.

(10) Patent No.: US 11,169,147 B2
(45) Date of Patent: Nov. 9, 2021

(54) METHOD FOR IMMOBILIZING PROTEIN ON PARTICLE

(71) Applicant: AMOLIFESCIENCE CO., LTD., Seoul (KR)

(72) Inventors: Sung-Il Kim, Gangwon-do (KR); Seam Mun, Gangwon-do (KR)

(73) Assignee: AMOLIFESCIENCE CO., LTD., Seoul (KR)

( * ) Notice: Subject to any disclaimer, the term of this patent is extended or adjusted under 35 U.S.C. 154(b) by 256 days.

(21) Appl. No.: 15/769,729

(22) PCT Filed: Oct. 21, 2016

(86) PCT No.: PCT/KR2016/011931
§ 371 (c)(1),
(2) Date: Apr. 19, 2018

(87) PCT Pub. No.: WO2017/069583
PCT Pub. Date: Apr. 27, 2017

(65) Prior Publication Data
US 2018/0313824 A1 Nov. 1, 2018

(30) Foreign Application Priority Data
Oct. 23, 2015 (KR) .................. 10-2015-0147960

(51) Int. Cl.
| G01N 33/531 | (2006.01) |
| G01N 33/553 | (2006.01) |
| B01J 31/12 | (2006.01) |
| G01N 33/543 | (2006.01) |
| B01J 31/02 | (2006.01) |

(52) U.S. Cl.
CPC ........ *G01N 33/531* (2013.01); *B01J 31/0247* (2013.01); *B01J 31/12* (2013.01); *G01N 33/54353* (2013.01); *G01N 33/553* (2013.01); *B01J 2231/34* (2013.01)

(58) Field of Classification Search
CPC ............... G01N 33/531; G01N 33/553; G01N 33/54353; B01J 19/10; B01J 31/12; B01J 31/0247; B01J 2231/34
USPC ......................................... 436/501, 525, 527
See application file for complete search history.

(56) References Cited

U.S. PATENT DOCUMENTS

| 2014/0206822 A1 | 7/2014 | Joo et al. |
| 2015/0125533 A1* | 5/2015 | Sallam ............... A61K 41/0052 424/490 |

FOREIGN PATENT DOCUMENTS

| CN | 103472219 | 12/2013 | |
| CN | 104374909 | 2/2015 | |
| KR | 10-2013-0000457 | 1/2013 | |
| KR | 10-2014-0106268 | 9/2014 | |
| KR | 10-2015-0054543 | 5/2015 | |
| WO | WO2013/014538 A2 | 1/2013 | |
| WO | WO-2013014538 A2 * | 1/2013 | ............. A61K 47/02 |

OTHER PUBLICATIONS

Sharma et al."Rapid Immobilization of Enzymes onto Solid Supports by Ultrasound Waves", Artificial Cells, Blood Substitutes & Biotechnology (2011), 39(5):289-292 (Year: 2011).*
Kerwin "Polysorbates 20 and 80 Used in the formulation of Protein Biotherapeutics: Structure and Degredation Pathways", Journal of Pharmaceutical Sciences (2008) 97(8):2924-2935 (Year: 2008).*
Kerwin, "Polysorbates 20 and 80 Used in the Formulation of Protein Biotherapeutics: Structure and Degradation Pathways," Journal of Pharmaceutical Sciences, vol. 97, No. 8 (2008), pp. 2924-2935.
Sharma, et al., "Ultrasound wave-mediated enzyme-linked immunosorbent assay technique," Analytica Chimica Acta 650 (2009) pp. 241-246.
Office Action dated Jul. 26, 2019, in Chinese Patent Application No. 2016800619729, English Translation and Full Reference.

* cited by examiner

*Primary Examiner* — Galina M. Yakovleva
(74) *Attorney, Agent, or Firm* — Wells St. John P.S.

(57) ABSTRACT

This invention relates to a method of immobilizing a protein on particles, and more particularly to a method of immobilizing an antibody on magnetic particles. The method of immobilizing the protein on the particles can prevent aggregation due to non-specific binding between proteins and between proteins and particles, whereby a relatively small amount of protein can be immobilized on particles.

4 Claims, 4 Drawing Sheets

METHOD FOR IMMOBILIZING PROTEIN ON PARTICLE

CROSS REFERENCE TO RELATED APPLICATION

This is a 35 U.S.C. § 371 application of, and claims priority to, International Application No. PCT/KR2016/011931, which was filed on Oct. 21, 2016, and claims priority to KR Patent Application No. 10-2015-0147960, which was filed on Oct. 23, 2015, the teachings of the applications of which are incorporated herein by reference.

TECHNICAL FIELD

The present invention relates to a method of immobilizing a protein on particles, and more particularly to a method of immobilizing an antibody on magnetic particles.

BACKGROUND ART

Protein-immobilized particles for immunochromatographic analysis are used to identify diseases or detect changes thereof in fields of healthcare and are also utilized to simply analyze small amounts of analytes in various fields, including food and biological processing, environmental fields, and the like. Particularly, in the field of healthcare, the range of application thereof has expanded to pregnancy, ovulation, infectious diseases, drug abuse, acute myocardial infarction, cancer, and the like. For example, the above particles may be employed in the separation of disease markers in the blood.

Among the particles, magnetic particles are receiving attention as a labeling material for binding assays because of advantages such as easy control, high biocompatibility and high sensitivity. For example, Korean Patent Application Publication No. 2014-0106268 discloses a method of detecting biomolecules using magnetic particles.

Meanwhile, a method of immobilizing a protein on particles is performed in a manner in which the surface of particles is modified so that a carboxyl group (—COOH) is immobilized on the surface of the particles, followed by immobilization through amide bonding with an amino group (—NH$_2$) of a protein. As representative examples of the above method, a method of immobilizing a protein on particles using Magnabind available from Thermo and a method of immobilizing a protein on particles using Dynabeads Myone™ available from Life Technology are known. However, the protein immobilization methods of Thermo and Life Technology are problematic in that protein-protein aggregates or protein-particle aggregates may form due to non-specific binding thereof, and the method of Life Technology has a disadvantage because the processing time is long. Hence, there is a continuing need for a method of immobilizing a protein on particles that is able to overcome such disadvantages.

DISCLOSURE

Technical Problem

Accordingly, the present invention is intended to provide a method of immobilizing a protein on particles, in which a relatively small amount of protein may be immobilized while solving the problems encountered in the related art, such as long processing time and aggregation due to non-specific binding between proteins and between proteins and particles.

Technical Solution

Therefore, the present invention provides a method of immobilizing a protein on particles, comprising: modifying the surface of particles so that a carboxyl group (—COOH) is immobilized on the surface of the particles subjecting the modified particles to protein addition and then sonication; and immobilizing a protein on the surface of the particles by adding a catalyst for promoting amide bonding between the carboxyl group immobilized on the surface of the particles and an amino group (—NH$_2$) of the protein after the sonication, wherein during the immobilizing the protein on the surface of the particles, sonication is carried out and thereby non-specific adsorption between proteins or between proteins and magnetic particles is prevented.

In another embodiment of the present invention, the modified particles may be subjected to sonication after the modifying the surface of the particles and before the subjecting the modified particles to protein addition and then sonication.

In still another embodiment of the present invention, during the immobilizing the protein on the surface of the particles, a surfactant may be added together with the catalyst for promoting amide bonding.

In yet another embodiment of the present invention, the particles may be magnetic particles.

In still yet another embodiment of the present invention, the particles may have a size ranging from 100 nm to 3 μm.

In a further embodiment of the present invention, the protein may be an antibody, and the antibody may be immobilized on the particles through amide bonding between the carboxyl group immobilized on the surface of the particles and an amino group (—NH$_2$) of a constant region of a heavy chain of the antibody.

In still a further embodiment of the present invention, the catalyst for promoting amide bonding may be at least one selected from the group consisting of EDC (1-ethyl-3-(3-dimethylaminopropyl)carbodiimide hydrochloride), CDI (N,N'-carbonyldiimidazole) and DOC (dicyclohexylcarbodiimide).

Advantageous Effects

According to the present invention, a method of immobilizing a protein on particles can prevent aggregation due to non-specific binding between proteins and between proteins and particles, whereby a relatively small amount of protein can be immobilized on particles.

MODE FOR INVENTION

Figure 1:
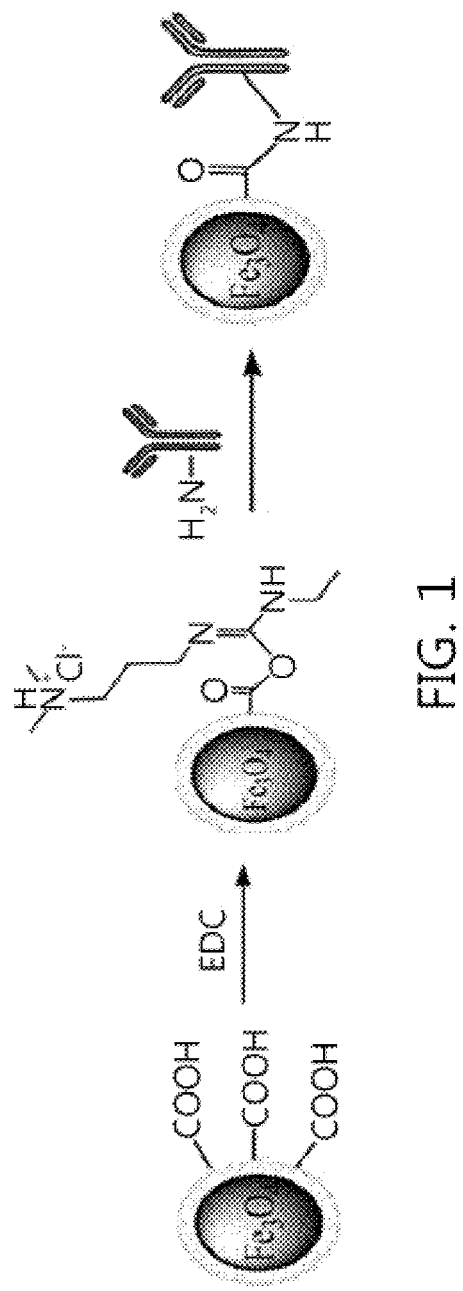
FIG. 1 schematically shows the typical process of immobilizing an antibody on particles.

The present invention relates to a method of immobilizing a protein on particles, and more particularly to a method of immobilizing an antibody on magnetic particles. The method of the present invention may prevent aggregation due to non-specific binding between proteins and between proteins and particles using sonication and a surfactant, whereby a relatively small amount of protein may be immobilized on particles.

Hereinafter, a detailed description will be given of the present invention.

The present invention addresses a method of immobilizing a protein on particles, comprising the steps of modifying the surface of particles so that a carboxyl group (—COOH) is immobilized on the surface of the particles; subjecting the modified particles to sonication, protein addition and then sonication; and immobilizing a protein on the surface of the particles by adding a catalyst for promoting amide bonding between the carboxyl group immobilized on the surface of the particles and the amino group (—NH$_2$) of the protein after the sonication, wherein during the step of immobilizing the protein on the surface of the particles, sonication is carried out and thereby non-specific adsorption between proteins or between proteins and magnetic particles is prevented.

The sonication functions to prevent non-specific adsorption between proteins and between proteins and particles and also to uniformly immobilize the protein on the particles. The sonication is carried out after the step of modifying the surface of the particles, after the protein addition step, and during the step of immobilizing the protein on the surface of the particles by adding the catalyst, and the number of sonication processes is not particularly limited during the individual steps. For example, sonication may be performed seven times at intervals of 5 min during the step of immobilizing the protein on the surface of the particles by adding the catalyst.

In the step of immobilizing the protein on the surface of the particles, a surfactant (detergent) may be added together with the catalyst for promoting amide bonding. The surfactant plays a role in preventing electrostatic binding of proteins and non-specific binding between proteins and magnetic particles. The surfactant is not particularly limited, so long as it is able to prevent the non-specific binding, and at least one selected from the group consisting of anionic, cationic, amphoteric and nonionic surfactants may be used. For example, T-20 or SDS may be used as the surfactant. The surfactant may also be used during the step of modifying the surface of the particles so that the carboxyl group (—COOH) is immobilized on the surface of the particles.

The particles may be magnetic particles. The magnetic particles of the present invention are not particularly limited so long as they may be applied to magnetophoresis according to conventional techniques, and are preferably magnetic particles including $Fe_2O_3$ or $Fe_3O_4$. The size of the particles is preferably 100 nm to 3 μm, and more preferably 100 to 400 nm.

The protein may be an antibody. As used herein, the term "antibody", as known in the art, refers to a specific protein molecule able to bind to a specific antigen or epitope thereof through a specific reaction, and may include an immunoglobulin molecule having binding ability to an antigen (e.g. monoclonal antibody, polyclonal antibody, etc.), fragments of the immunoglobulin molecule (e.g. Fab', F(ab')2, Fab, Fv, rIgG, single-chain Fv fragment (scFv), etc.), and the like. In particular, the immunoglobulin molecule has a heavy chain and a light chain, and each of the heavy chain and the light chain includes a constant region and a variable region (the region is also known as a "domain"), and the variable region of the light chain and the heavy chain includes three variable complementarity-determining regions (CDRs), which are able to bind to the epitope of the antigen; and four "framework regions (FRs)". The CDR of each chain is typically called CDR1, CDR2, and CDR3, respectively, sequentially from the N-terminus, and is identified by the chain in which specific CDR is positioned.

From the morphological aspects of the antibody, the antibody preferably includes a natural antibody such as IgG, IgM, IgA, IgE, IgD, IgT, IgY, a single-chain antibody, etc. specific to the antigen; a recombinant antibody configured to include some of the natural antibody; and a mutant antibody in which some of the natural antibody is mutated in order to decrease the dissociation constant of an antibody to an antigen, reduce the rejection reaction to an antibody in vivo, or increase antibody stability, and more preferably includes a natural antibody such as IgG, a mutant antibody mutated to decrease the dissociation constant of an antibody to an antigen, a recombinant antibody including a GDR (complementarity-determining region) directly binding to an antigen, or fragments thereof.

The immobilization of the antibody on the particles may be realized through amide bonding between the carboxyl group immobilized on the surface of the particles and the amino group (—NH$_2$) of the constant region (e.g. lysine) of the heavy chain of the antibody.

In the method of immobilizing the protein on the particles, the surface of the particles is modified so that the carboxyl group is immobilized on the surface of the particles, and this process is performed in order to realize immobilization through amide bonding with the antibody having an amide group. The surface modification of the particles may be performed by the methods known in the art. For example, only sodium citrate may be applied to the surface of the particles, or the particles may be coated with silica and then treated with APTES (aminopropyl triethoxysilane) so that the terminal amino group is treated with glutaric anhydride to thus immobilize the carboxyl group. The surface modification of the particles has to be carried out at a temperature not exceeding 40° C., and preferably at room temperature, in order to prevent protein denaturation. Also, the reaction time is set to 30 min, and ultrasonic waves may be applied for ones of seconds at intervals of 5 min.

The catalyst for promoting amide bonding is added after the sonication, and the catalyst functions to promote amide bonding between the carboxyl group immobilized on the surface of the particles and the amino group (—NH$_2$) of the protein. Thus, the catalyst may be used without particular limitation so long as it functions to promote the amide bonding. The catalyst is preferably at least one selected from the group consisting of EDC (1-ethyl-3-(3-dimethylaminopropyl)carbodiimide hydrochloride), CDI (N,N'-carbonyldiimidazole) and DOC (dicyclohexylcarbodiimide).

The catalyst for promoting amide bonding may be added in an appropriate amount and then mixed at room temperature for 5 to 60 min to thus immobilize the protein on the surface of the particles, and sonication may be carried out as described above, thereby preventing non-specific adsorption between proteins or between proteins and magnetic particles.

The protein-immobilized particles manufactured by the above method may be used in the fields of food and biological processing, the environment, healthcare and the like. In particular, the magnetic particles have magnet-attracting properties and are thus moved along the direction to which an external magnetic field is applied. When an antibody is immobilized on the magnetic particles, reaction thereof after movement to the desired position becomes possible, whereby biomolecules may be rapidly detected in the field of healthcare.

A better understanding of the present invention will be given through the following examples, which are merely set forth to illustrate, but are not to be construed as limiting the present invention and may be variously altered and changed.

Example 1. Preparation of Protein-Immobilized Particles 1 ml of 20 mg/ml magnetic particles (AMO-Mag, available from AMOGREENTECH) was washed three times with 1~5 ml of PBS (potassium-buffered saline). Thereafter, 225 μl of PBS and 225 μl of a mixed solution (pH 4.7 0.1M MES+0.9% NaCl+0.02% T-20; addition of a surfactant T-20 in order to prevent aggregation due to electrostatic binding of proteins and non-specific binding between proteins and magnetic particles) were added thereto, after which sonication was sufficiently performed, and 1 mg or 2 mg of IgG (immunoglobulin G), namely an anti-RBC (red blood cell) antibody (made by Fitzgerald), was added thereto, after which sonication was performed again.

Next, 50 μl of 10 mg/ml EDC (1-ethyl-3-(3-dimethylaminopropyl)carbodiimide hydrochloride) dissolved in the mixed solution (pH 4.7 0.1M MES+0.9% NaCl+0.02% T-20) was added thereto, and then mixed at room temperature for 30 min (sonication was performed at intervals of 5 min after initial sonication). Subsequently, washing three times with 1 ml of PBS and final storage in PBST (PBS+0.1% T-20) were performed, thereby preparing protein-immobilized particles.

Comparative Example 1. Preparation of Protein-Immobilized Particles Preparation Method by Thermo 1 ml of 20 mg/ml magnetic particles (Magnabind, available from Thermo) was washed three times with 1 ml of PBS. Next, 5~10 mg of IgG and a reaction solution comprising pH 4.7 0.1M MES (2-(N-morpholino)ethanesulfonic acid) and 0.9% NaCl were added to 20 mg of the washed magnetic particles, and 100 μl of 10 mg/ml EDC was then added thereto, followed by mixing at room temperature for 30 min. Thereafter, washing was performed three times with 1 ml of PBS, thereby obtaining protein-immobilized particles.

Comparative Example 2. Preparation of Protein-Immobilized Particles Preparation Method by Life Technology 100 μl of 10 mg/ml magnetic particles (Dynabeads Myone, available from Life Technology) was added to pH 6.0 15 mM MES, and 10 μl of 10 mg/ml EDC was then added thereto, followed by mixing at room temperature for 30 min. Thereafter, magnetic collection and then removal of a supernatant were performed, and 200~500 μl of pH 6.0 15 mM MES was added with 0.4 mg of IgG and then mixed at room temperature overnight. Thereafter, washing three times with 1 ml of PBST (PBS+0.1% T-20) and final storage in PBSTB (PBS+0.1% T-20+0.1% BSA) were conducted, thereby preparing protein-immobilized particles.

Text Example 1. Test of Separation of Erythrocytes Using Protein-Immobilized Particles The protein-immobilized particles (50 μl) of Example 1 (1 mg of protein-immobilized particles) and Comparative Example 1 (4 mg or 6 mg of protein-immobilized particles) were added to 50 μl of a blood sample and were then allowed to react at room temperature for about 5 min. The results are shown in FIGS. 2 to 7.

Figure 2:
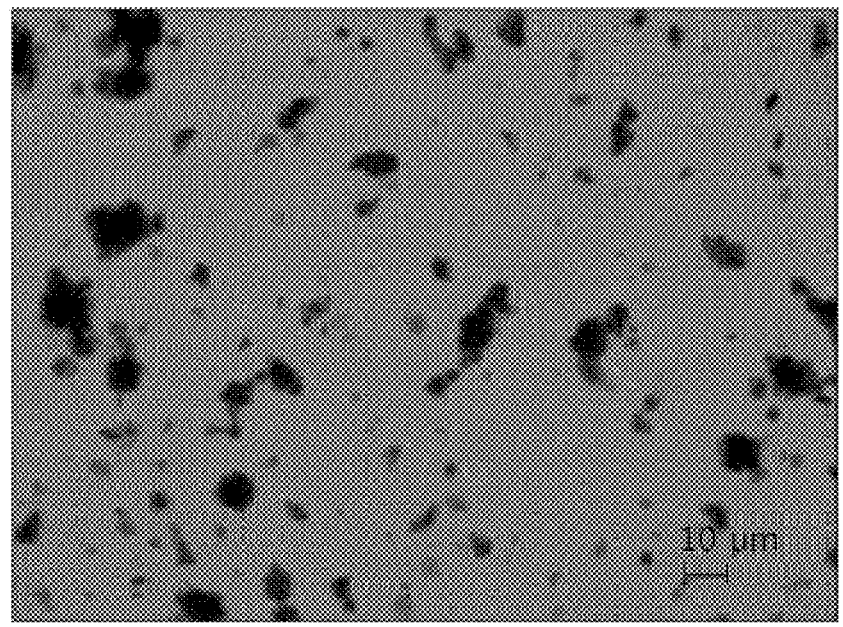
FIG. 2 shows the results of observation using a phase-difference microscope when a blood sample is added with 6 mg of protein-immobilized particles of Comparative Example 1.

FIG. 2 shows the results of observation using a phase-difference microscope when a blood sample is added with 6 mg of the protein-immobilized particles of Comparative Example 1.

Figure 3:
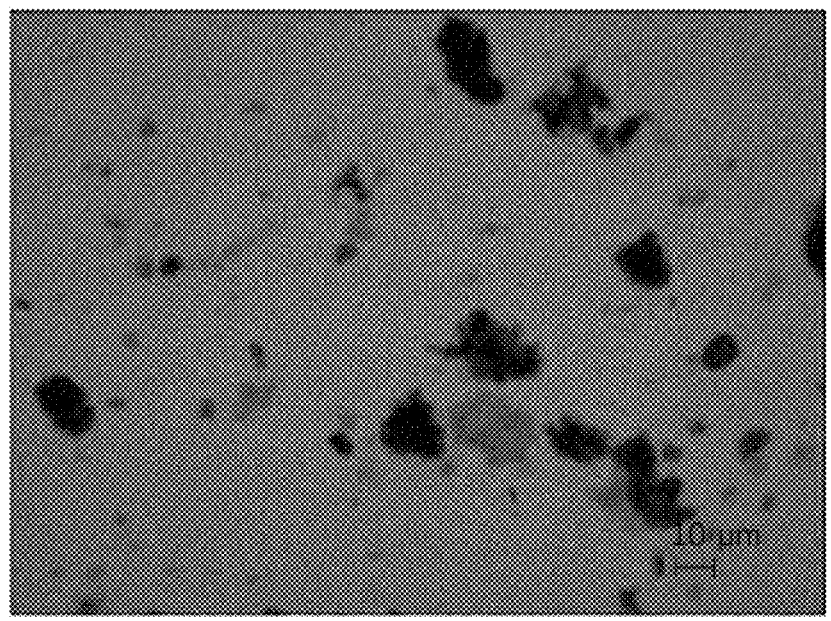
FIG. 3 shows the results of observation using a phase-difference microscope when a blood sample is added with 4 mg of protein-immobilized particles of Comparative Example 1.

FIG. 3 shows the results of observation using a phase-difference microscope when a blood sample is added with 4 mg of the protein-immobilized particles of Comparative Example 1.

Figure 4:
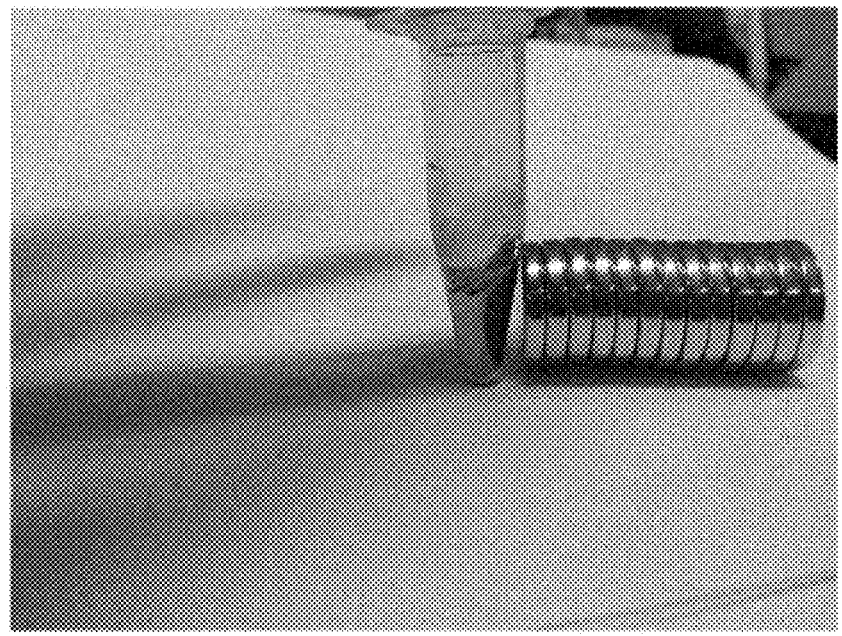
FIG. 4 shows the results of separation of erythrocytes using a magnet after addition of a blood sample with 6 mg of protein-immobilized particles of Comparative Example 1.

FIG. 4 shows the results of separation of erythrocytes using a magnet after addition of a blood sample with 6 mg of the protein-immobilized particles of Comparative Example 1.

Figure 5:
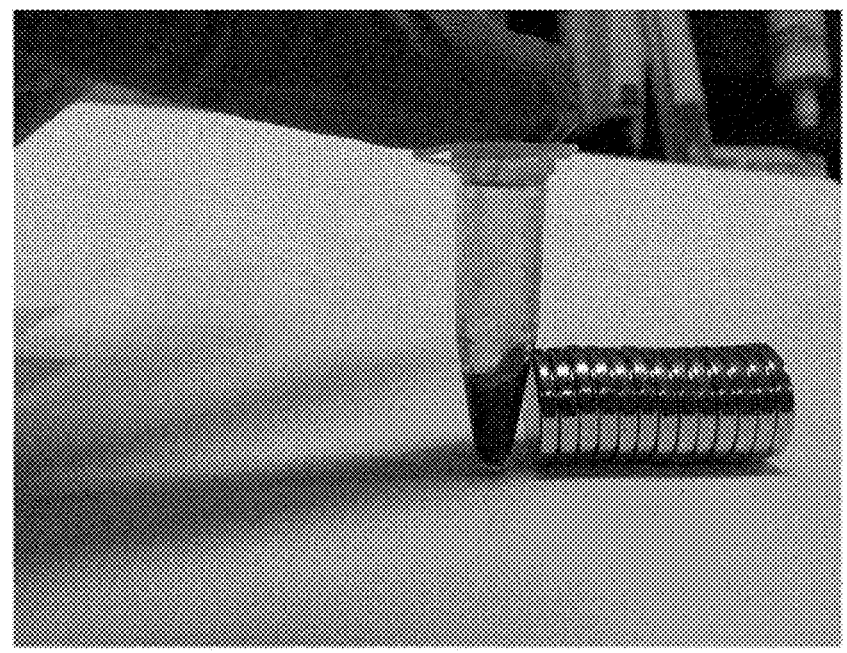
FIG. 5 shows the results of separation of erythrocytes using a magnet after addition of a blood sample with 4 mg of protein-immobilized particles of Comparative Example 1.

FIG. 5 shows the results of separation of erythrocytes using a magnet after addition of a blood sample with 4 mg of the protein-immobilized particles of Comparative Example 1.

Figure 6:
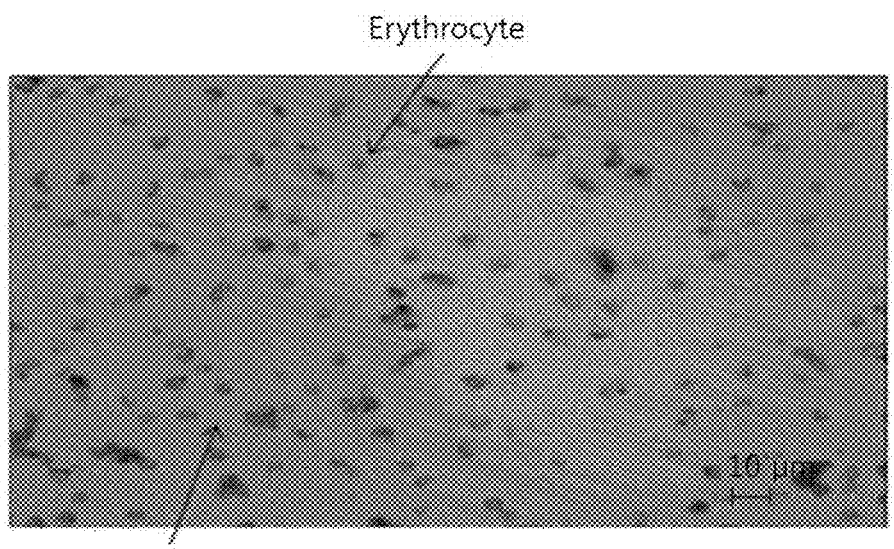
FIG. 6 shows the results of observation using a phase-difference microscope when a blood sample is added with 1 mg of protein-immobilized particles of Example 1.

FIG. 6 shows the results of observation using a phase-difference microscope when a blood sample is added with 1 mg of the protein-immobilized particles of Example 1.

Figure 7:
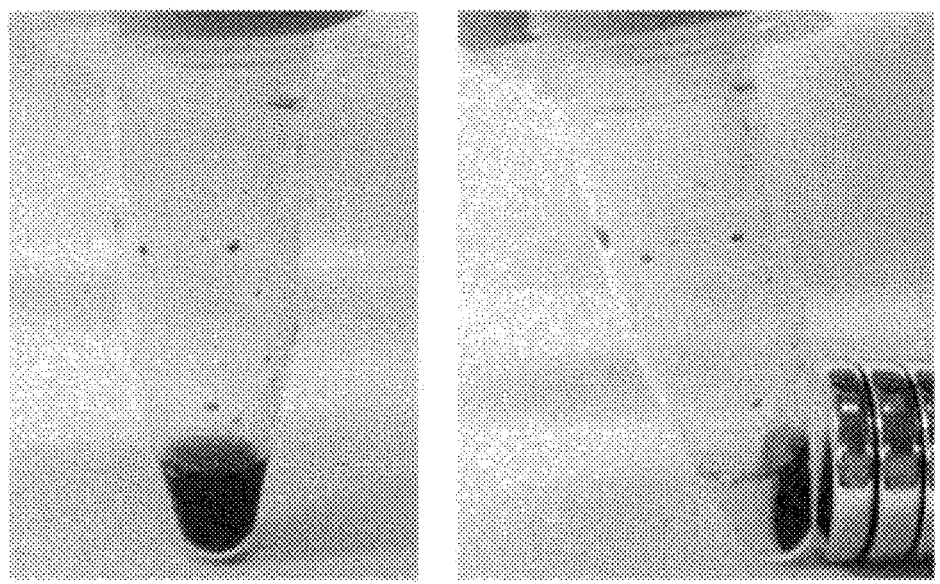
FIG. 7 shows the photograph (left) after addition of a blood sample with 1 mg of protein-immobilized particles of Example 1 and the results (right) of separation of erythrocytes using a magnet.

FIG. 7 shows the photograph (left) after addition of a blood sample with 1 mg of the protein-immobilized particles of Example 1 and the results (right) of separation of erythrocytes using a magnet.

As shown in FIGS. 2 to 7, the protein-immobilized particles of Comparative Example 1 were aggregated into large groups that appeared black, and erythrocytes were separated by magnetic particles when the protein-immobilized particles were added in an amount of 6 mg. However, the protein-immobilized particles of Example 1 were hardly aggregated, and even when the protein-immobilized particles were added in an amount of 1 mg, which is smaller than 6 mg as above, all erythrocytes were separated. In particular, as shown in FIG. 7, compared to Comparative Example 1, the color of the wall of tube of Example 1 was clean, from which the particles were confirmed to react with the target material in the blood without non-specific adsorption.

The invention claimed is:

1. A method of immobilizing an anti-red blood cell antibody on particles, comprising:
    modifying a surface of particles so that a carboxyl group (—COOH) is immobilized on the surface of the particles;
    subjecting the modified particles to an anti-red blood cell antibody addition and then sonication; and
    after the sonication, immobilizing an anti-red blood cell antibody on the surface of the particles by adding a catalyst for promoting amide bonding between the carboxyl group immobilized on the surface of the particles and an amino group (—NH$_2$) of the anti-red blood cell antibody and further performing the sonication, wherein during the immobilizing the anti-red blood cell antibody on the surface of the particles, sonication is carried out and thereby non-specific adsorption between anti-red blood cell antibodies or between anti-red blood cell antibodies and magnetic particles is prevented, wherein during the modifying the surface of particles, a surfactant is added and during the immobilizing the anti-red blood cell antibody on the surface of the particles, the surfactant is added together with the catalyst for promoting amide bonding, wherein the particles are magnetic particles and have a size ranging from 100 nm to 400 nm, and using the protein-immobilized magnetic particles to separate erythrocytes from a blood sample.

2. The method of claim 1, wherein the modified particles are subjected to sonication after the modifying the surface of the particles and before the subjecting the modified particles to anti-red blood cell antibody addition and then sonication.

3. The method of claim 1, wherein the anti-red blood cell antibody is immobilized on the particles through amide bonding between the carboxyl group immobilized on the surface of the particles and an amino group (—NH$_2$) of a constant region of a heavy chain of the antibody.

4. The method of claim 1, wherein the catalyst for promoting amide bonding is at least one selected from the group consisting of EDC (1-ethyl-3-(3-dimethylaminopropyl)carbodiimide hydrochloride), CDI (N,N'-carbonyldiimidazole), and DOC (dicyclohexylcarbodiimide).

* * * * *